(12) United States Patent
Otake

(10) Patent No.: US 11,819,630 B2
(45) Date of Patent: Nov. 21, 2023

(54) CATHETER AND CATHETER ASSEMBLY

(71) Applicant: TERUMO KABUSHIKI KAISHA, Tokyo (JP)

(72) Inventor: Yuya Otake, Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 389 days.

(21) Appl. No.: 17/154,403

(22) Filed: Jan. 21, 2021

(65) Prior Publication Data
US 2021/0138192 A1    May 13, 2021

Related U.S. Application Data

(62) Division of application No. 16/135,184, filed on Sep. 19, 2018, now Pat. No. 10,940,288.

(30) Foreign Application Priority Data

Sep. 21, 2017    (JP) .................................. 2017-181455

(51) Int. Cl.
*A61M 25/01*    (2006.01)
*A61M 25/00*    (2006.01)

(52) U.S. Cl.
CPC .... *A61M 25/0053* (2013.01); *A61M 25/0023* (2013.01); *A61M 25/0041* (2013.01);
(Continued)

(58) Field of Classification Search
CPC ...... A61M 25/0041; A61M 2025/0004; A61M 2025/0175
See application file for complete search history.

(56) References Cited

U.S. PATENT DOCUMENTS

2002/0087076 A1    7/2002    Meguro et al.
2006/0089618 A1    4/2006    McFerran et al.
(Continued)

FOREIGN PATENT DOCUMENTS

CN    104922786 A    9/2015
CN    105492060 A    4/2016
(Continued)

OTHER PUBLICATIONS

Office Action (Second Office Action) dated Mar. 17, 2022, by the State Intellectual Property Office of People's Republic of China in corresponding Chinese Patent Application No. 201811055997.5 and an English Translation of the Office Action. (24 pages).
(Continued)

*Primary Examiner* — Laura A Bouchelle
(74) *Attorney, Agent, or Firm* — BUCHANAN INGERSOLL & ROONEY PC

(57) ABSTRACT

A treatment method is disclosed, which includes preparing a catheter assembly by inserting an inner catheter into an outer catheter and screwing a protrusion of the outer catheter into a helical groove of the inner catheter; introducing the catheter assembly into the radial artery along a guide wire; pushing the catheter assembly along the guide wire to a target site in front of a stenosis of a blood vessel; releasing the screwing between the helical groove of the inner catheter and the protrusion of the outer catheter after a distal end of the catheter assembly reaches the target site; and causing the outer catheter to abut on at least a part of wall surfaces of a thoracic aorta and an abdominal aorta while drawing a helix and causing the treatment device to protrude from a distal end of the outer catheter at the stenosis.

20 Claims, 8 Drawing Sheets

(52) U.S. Cl.
CPC ..... *A61M 25/0102* (2013.01); *A61M 25/0067* (2013.01); *A61M 25/0105* (2013.01); *A61M 2025/0004* (2013.01); *A61M 2025/0175* (2013.01)

(56) References Cited

U.S. PATENT DOCUMENTS

| | | |
|---|---|---|
| 2007/0167924 A1 | 7/2007 | Benjamin et al. |
| 2008/0264993 A1 | 10/2008 | Schulte et al. |
| 2012/0179111 A1 | 7/2012 | Fojtik |
| 2012/0179140 A1 | 7/2012 | Fojtik |
| 2014/0261407 A1 | 9/2014 | Roberts et al. |
| 2014/0358123 A1 | 12/2014 | Ueda et al. |
| 2015/0265798 A1 | 9/2015 | Nihonmatsu et al. |
| 2017/0128639 A1 | 5/2017 | Erbey, III et al. |
| 2017/0348512 A1 | 12/2017 | Orr et al. |
| 2018/0214667 A1 | 8/2018 | Lederman et al. |
| 2019/0083743 A1 | 3/2019 | Otake |

FOREIGN PATENT DOCUMENTS

| | | | | |
|---|---|---|---|---|
| CN | 106039526 A | 10/2016 | | |
| JP | 2002-143318 A | 5/2002 | | |
| JP | 2012-055601 A | 3/2012 | | |
| JP | 2014230710 A | 12/2014 | | |
| JP | 2016-112201 A | 6/2016 | | |
| WO | 2015/146408 A1 | 10/2015 | | |
| WO | 2015146651 A1 | 10/2015 | | |
| WO | WO-2015146408 A1 * | 10/2015 | ............. | A61F 2/958 |
| WO | 2016/186880 A1 | 11/2016 | | |

OTHER PUBLICATIONS

Office Action (Notice of Reasons for Refusal) dated Apr. 20, 2021, by the Japanese Patent Office in corresponding Japanese Patent Application No. 2017-181455 and an English Translation of the Office Action. (6 pages).

Office Action (Rejection Decision) dated Jul. 18, 2022, by the National Intellectual Property Administration, P. R. China in corresponding Chinese Patent Application No. 201811055997.5 and an English Translation of the Office Action. (18 pages).

The extended European Search Report dated Feb. 4, 2019, by the European Patent Office in corresponding European Patent Application No. 18194591.6-1135, 11 pages.

Office Action (First Office Action) dated Jul. 22, 2021, by the State Intellectual Property Office of People's Republic of China in corresponding Chinese Patent Application No. 201811055997.5 and an English Translation of the Office Action. (16 pages).

* cited by examiner

CATHETER AND CATHETER ASSEMBLY

CROSS-REFERENCES TO RELATED APPLICATIONS

This application is a divisional application of U.S. patent application Ser. No. 16/135,184 filed on Sep. 19, 2018, which claims priority to Japanese Application No. 2017-181455 filed on Sep. 21, 2017, the entire content of both of which is incorporated herein by reference.

TECHNICAL FIELD

The present disclosure generally relates to a catheter and a catheter assembly.

RELATED ART

In recent years, a technique known as Trans Radial Intervention (TRI), which can perform a treatment by introducing a catheter from an artery (a radial artery or a brachial artery) of an arm has attracted attention since a physical burden on a patient is relatively small and the patient can be discharge from the hospital sooner.

For example, JP 2014-230710 A describes a technique that performs treatment by introducing a catheter from an artery of an arm and delivering the elongated catheter to a lesion of, for example, peripheral arterial disease (PAD) formed in a blood vessel of a lower limb.

As described in JP 2014-230710 A, the catheter delivered to the lesion in a blood vessel of a lower limb via the artery of the arm has a relatively long length in the longitudinal direction. When handling such a catheter having the relatively long length in the longitudinal direction, a surgeon takes a measure by winding the catheter and bundling the catheter with a clip or the like in order to prevent the catheter from being in contact with an unclean surface such as a floor, for example. In this manner, the surgeon needs to pay attention such that the catheter is not brought into contact with an unclean surface when using a catheter whose length in the longitudinal direction is relatively long.

SUMMARY

A catheter and a catheter assembly are disclosed, which are relatively easy to handle.

A catheter is disclosed, which includes: an elongated shaft configured to be inserted into a body lumen; and a hub connected to a proximal end side of the shaft. The shaft forms a first shape at least a part of which is wound in a state where the shaft is suspended in a gravity direction by holding the hub, and forms a second shape at least a part of which is wound and in which a length of the shaft along the gravity direction is shorter than a length of the shaft along the gravity direction in the first shape in a state where the hub and the shaft are placed on a flat reference plane perpendicular to the gravity direction.

A catheter assembly is disclosed having an outer catheter and an inner catheter insertable into the outer catheter, each of the outer catheter and the inner catheter including an elongated shaft and a hub connected to a proximal end side of the shaft. The shaft of at least one catheter of the outer catheter and the inner catheter forms a first shape at least a part of which is wound in a state where the shaft is suspended in a gravity direction by holding the hub of the one catheter, and forms a third shape in which at least a part of the shafts of the outer catheter and the inner catheter is wound in a state where the inner catheter is inserted into the outer catheter, the shafts of the outer catheter and the inner catheter are suspended in the gravity direction by holding the hub of the outer catheter or the inner catheter.

According to the catheter configured as described above, when a surgeon holds and manipulates a proximal end side of the catheter, at least a part of the shaft is wound to form the first shape and becomes compact. Thus, a risk of the catheter being in contact with an unclean surface such as a floor can be reduced, and it becomes unnecessary or easier for the surgeon to perform work of bundling the catheter with a clip or the like so as to prevent the contact with the unclean surface, for example, such as the floor. In addition, when the surgeon places the catheter on a medical tray, a table, or the like, at least a part of the shaft forms the second shape and becomes more compact than in the suspended state. In this manner, it is possible to provide a catheter which is relatively easy to handle.

According to the catheter assembly configured as described above, when a surgeon holds and manipulates a proximal end side of the catheter assembly in a state where the inner catheter is inserted into the outer catheter, at least a part of the shaft of the catheter assembly is wound to form the third shape and becomes relatively compact. Thus, a risk of the catheter assembly being in contact with an unclean surface such as a floor can be reduced, and it becomes unnecessary or relatively easy for the surgeon to perform work of bundling the catheter with a clip or the like so as to help prevent contact with an unclean surface such as the floor. In this manner, it is possible to provide the catheter assembly which is relatively easy to handle.

In accordance with an aspect, a catheter is disclosed comprising: an elongated shaft to be inserted into a body lumen; a hub connected to a proximal end side of the shaft, wherein the shaft forms a first shape at least a part of which is wound in a state where the shaft is suspended in a gravity direction by holding the hub; a portion, which is a half or more of the shaft from a distal end of the shaft to a distal end of the hub forms the first shape in the state where the shaft is suspended; and a hydrophilic coating layer is provided on at least a part of the distal end of the shaft such that a coating length of the hydrophilic coating layer is equal to or longer than ⅒ and equal to or smaller than ⅓ of a length from the distal end of the shaft to the distal end of the hub in a straight state.

In accordance with another aspect, a treatment method is disclosed comprising: preparing a catheter assembly by inserting an inner catheter into an outer catheter and screwing a protrusion of the outer catheter into a helical groove of the inner catheter; inserting a guide wire into a lumen of the inner catheter of the catheter assembly such that the guide wire protrudes from a distal end of the inner catheter; inserting the catheter assembly into an introducer sheath, the introducer sheath which pierces through and remains in a radial artery of a living body, in a state where the guide wire is inserted into a lumen of the catheter assembly; introducing the catheter assembly into the radial artery along the guide wire; pushing the catheter assembly to proceed along the guide wire to a target site in front of a stenosis of a blood vessel; releasing the screwing between the helical groove of the inner catheter and the protrusion of the outer catheter after a distal end of the catheter assembly reaches the target site; removing the inner catheter from the living body while leaving the outer catheter and the guide wire in the blood vessel; inserting a treatment device along the guide wire into a lumen of the outer catheter; and causing the outer catheter to abut on at least a part of wall surfaces of a thoracic aorta and an abdominal aorta while drawing a helix and causing the treatment device to protrude from a distal end of the outer catheter such that an expanded portion is arranged at the stenosis.

In accordance with a further aspect, a treatment method is disclosed comprising: inserting an inner catheter into an outer catheter and screwing a protrusion of the outer catheter into a helical groove of the inner catheter to form a catheter assembly; inserting a guide wire into a lumen of the inner catheter and protruding the guide wire from a distal end of the inner catheter; puncturing a radial artery of a living body with an introducer sheath; inserting a guide wire into a lumen of the catheter assembly; introducing the catheter assembly along with the guide wire into the radial artery via the introducer sheath; pushing the catheter assembly along the guide wire to a target site in a blood vessel; releasing the screwing between the helical groove of the inner catheter and the protrusion of the outer catheter after a distal end of the catheter assembly reaches the target site; removing the inner catheter from the living body while leaving the outer catheter and the guide wire in the blood vessel; inserting a treatment device along the guide wire into a lumen of the outer catheter; and causing the outer catheter to abut on at least a part of wall surfaces of a thoracic aorta and an abdominal aorta while drawing a helix and causing the treatment device to protrude from a distal end of the outer catheter at the target site.

DETAILED DESCRIPTION

Hereinafter, a catheter and a catheter assembly according to embodiments of the disclosure will be described with reference to the accompanying drawings. Incidentally, the following description does not limit the technical scope or the meaning of terms described in the claims. In addition, dimensional ratios of the drawings are exaggerated for the convenience of description and may differ from actual ratios in some cases.

Figure 1:
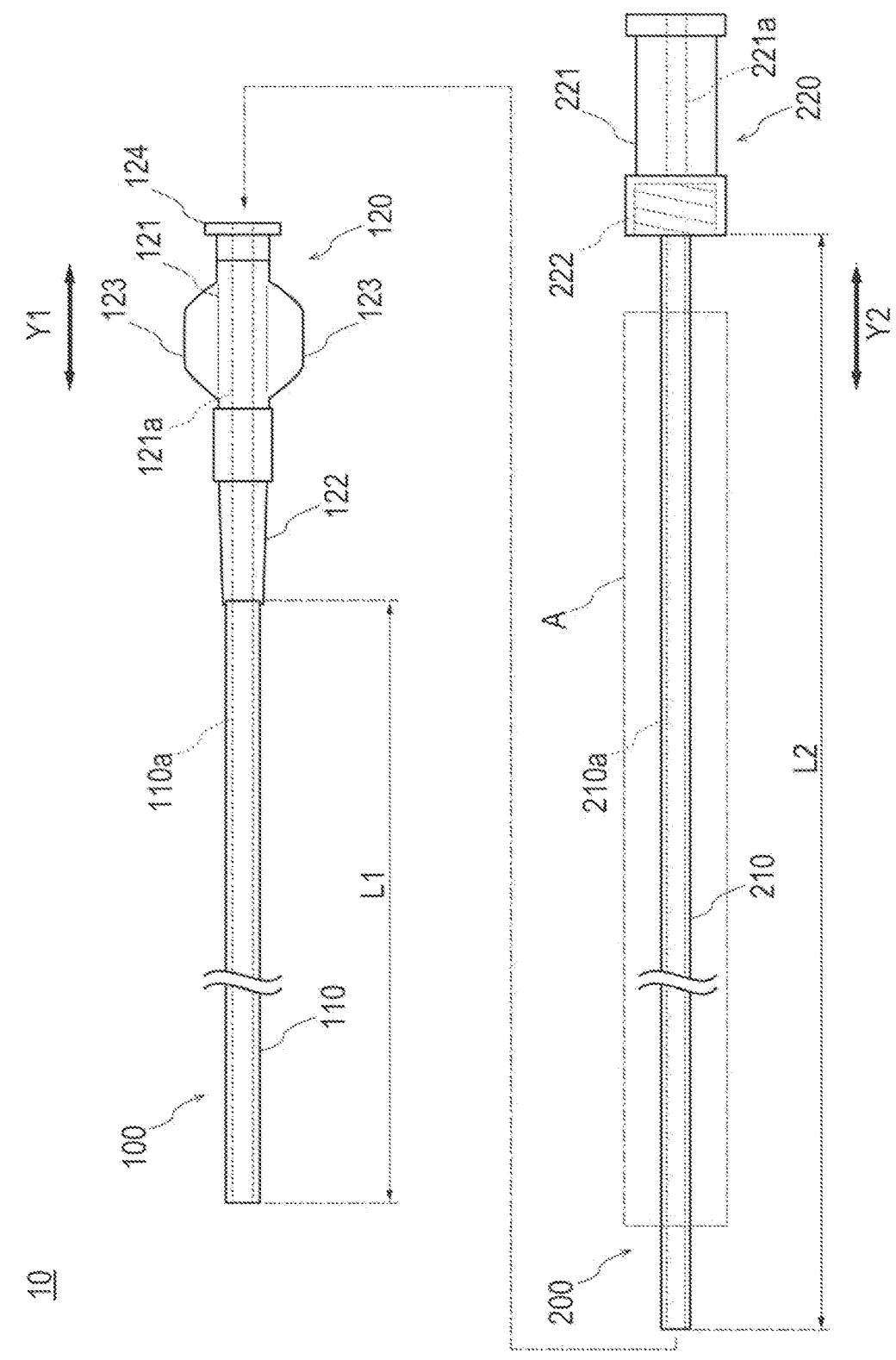
FIG. 1 is a schematic plan view illustrating a state where a catheter assembly stretched according to an embodiment of the disclosure.
Figure 2:
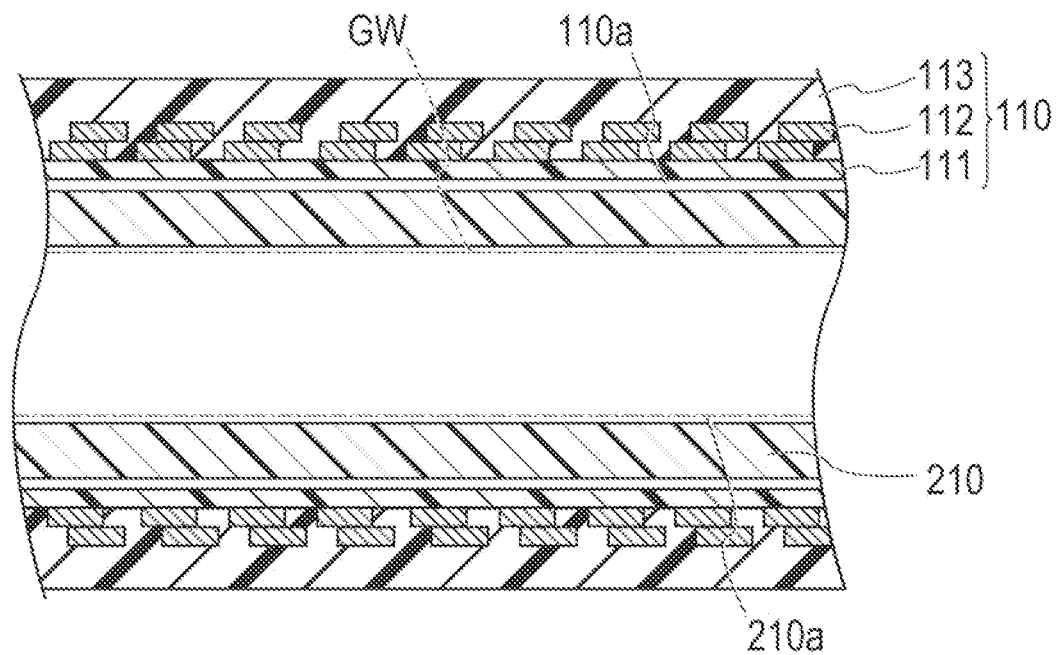
FIG. 2 is an enlarged cross-sectional view in a longitudinal direction of the catheter assembly according to the embodiment.

FIG. 1 is a view for describing the entire configuration of a catheter assembly 10 according to an embodiment. FIG. 2 is a view for describing each part of the catheter assembly 10. FIGS. 3A to 5 are views for describing shapes of an inner catheter 200 and the catheter assembly 10. FIG. 6 is a view for describing a use example of the catheter assembly 10.

The catheter assembly 10 is configured as a medical instrument (so-called guiding catheter) which is introduced into a blood vessel of a patient in advance in order to guide a medical instrument (for example, an image diagnostic catheter, a balloon catheter, or the like) for diagnosis and treatment to a lesion formed in the blood vessel of a lower limb via an artery of an arm of a patient.

As briefly described with reference to FIG. 1, the catheter assembly 10 includes an outer catheter 100 and an inner catheter 200 that is inserted into the outer catheter 100. Hereinafter, each part of the catheter assembly 10 will be described.

In the description of the present specification, a direction in which the outer catheter 100 extends when the outer catheter 100 is straightly stretched will be referred to as a "longitudinal direction Y1" as illustrated in FIG. 1. In addition, a direction in which the inner catheter 200 extends when the inner catheter 200 is straightly stretched will be referred to as a "longitudinal direction Y2". In addition, in the longitudinal directions Y1 and Y2 of the respective catheters 100 and 200, a side that is inserted into a body will be referred to as a "distal end side", a side opposite to the distal end side and on which the operation at hand is performed will be referred to as a "proximal end side". In addition, in each of the catheters 100 and 200, a distal end (most distal end) and the vicinity of the distal end (or most distal end) will be referred to as a "distal end portion", and a proximal end (most proximal end) and the vicinity of the proximal end (or most proximal end) will be referred to as a "proximal end portion".

Outer Catheter

The outer catheter 100 includes an elongated outer shaft 110 that is insertable into a blood vessel of a patient (corresponding to a "body lumen") and a hub 120 fixed to the proximal end portion of the outer shaft 110 and configured to be held and operated by a surgeon. Hereinafter, each part of the outer catheter 100 will be described.

First, the outer shaft 110 will be described.

The outer shaft 110 has a tubular member having flexibility (i.e., flexible tubular member). The outer shaft 110 has a lumen 110a formed over the entire length of the outer shaft 110. When the surgeon inserts the catheter assembly 10 into the blood vessel of the patient, the inner catheter 200 is inserted into the outer catheter 100 and a guide wire GW is inserted into the inner catheter 200 as illustrated in FIG. 6. After delivering the catheter assembly 10 to a target site so as to be guided by the preceding guide wire GW, the surgeon pulls the inner catheter 200 out of the living body (i.e., removes the inner catheter from the living body) and inserts a medical instrument for diagnosis and treatment (for example, an image diagnostic catheter, a balloon catheter, or the like) into the outer catheter to diagnose and treat the lesion. As described above, the inner catheter 200, the guide wire GW, the medical instrument for diagnosis and treatment, and the like can be inserted into the lumen 110a.

In the present embodiment, the outer shaft 110 has a tubular inner layer 111, a reinforcing member 112 provided on an outer circumferential surface of the inner layer 111, and an outer layer 113 covering (i.e., surrounding) the inner layer 111 and the reinforcing member 112 as illustrated in FIG. 2.

The material of the inner layer 111 can be a resin, for example, a fluorine-containing ethylenic polymer such as PTFE (polytetrafluoroethylene), PFA (tetrafluoroethylene-perfluoroalkyl vinyl ether copolymer), FEP (tetrafluoroethylene-hexafluoropropylene copolymer), and ETFE (ethylene-tetrafluoroethylene copolymer), polyamide such as nylon, or a polyamide elastomer such as a nylon elastomer. Among the above-described resins, it is preferable to use PTFE or PFA having a low frictional resistance as the material of the inner layer 111. As the inner layer 111 is made of such a material (i.e., PTFE or PFA having a low frictional resistance), a frictional resistance of an inner circumferential surface of the outer shaft 110 can be reduced, and the surgeon can smoothly move the medical instrument for diagnosis and treatment that has been inserted into the lumen 110a in the longitudinal direction Y1.

In the present embodiment, the reinforcing member 112 can be a plurality of strands (braid) braided in a mesh shape. The reinforcing member 112 can be provided (i.e., arranged) over the entire part of the outer shaft 110 excluding the distal end portion of the outer shaft 110. In this manner, the outer shaft 110 has the reinforcing member 112, and thus, has a relatively high kink resistance, a relatively high torque-transmitting property, and relatively high pushability.

The strand material of the reinforcing member 112 is not particularly limited, for example, a metal strand, a resin strand, a combination of the metal strand and the resin strand, or the like can be used. The metal strand material is not particularly limited, for example, stainless steel, tungsten, copper, nickel, titanium, a cobalt-chromium alloy, a nickel-titanium alloy (a super-elastic alloy), a copper-zinc alloy, an amorphous alloy, or the like can be used. The resin strand material is not particularly limited, for example, a hard polymer such as polyolefin, a liquid crystal polymer, or the like can be used. A sectional shape of the strand is not particularly limited, but can be formed in, for example, a substantially circular shape or a substantially rectangular shape. Meanwhile, it is preferable that the sectional shape of the strand be a substantially rectangular shape since the operability can be improved by increasing the density of the reinforcing member 112 on the outer shaft 110. In accordance with an exemplary embodiment, the reinforcing member 112 may be configured using a coil instead of braid.

The outer layer material 113 is not particularly limited, for example, a polymer material such as polyolefin (for example, polyethylene, polypropylene, polybutene, an ethylene-propylene copolymer, an ethylene-vinyl acetate copolymer, an ionomer, or a mixture of two or more kinds of these), polyvinyl chloride, polyamide, polyester, a polyester elastomer, a polyamide elastomer, polyurethane, a polyurethane elastomer, polyimide, fluorine resin, or a mixture of the materials can be used. Incidentally, the outer layer 113 may have a multilayer structure in which different resin materials are stacked or a segment structure in which different resin materials are continuously joined. In addition, the outer layer 113 may have a hydrophilic coating layer on an outer surface of the outer layer 113.

A length L1 of the outer shaft 110 from a distal end of the outer shaft 110 to a distal end of the hub 120 in the straight state (hereinafter simply referred to as the "length L1 of the outer shaft 110", see FIG. 1) is preferably 1200 mm to 2500 mm, and more preferably 1500 mm to 2000 mm such that the distal end of the outer shaft 110, which has been inserted from the artery of the arm, reaches the blood vessel of the lower limb.

In accordance with an exemplary embodiment, the length of the outer shaft 110 may be appropriately determined according to the size of the human body. In introducing from the radial artery, it is more preferable that the length of the outer shaft 110 is 1200 mm to 1400 mm in order to reach the iliac artery. In order to reach the superficial femoral artery from the radial artery, the length of the outer shaft 110 is preferably 1400 mm to 1600 mm, and the length of the outer shaft is preferably 1600 mm to 1800 mm for reaching the popliteal artery from the radial artery.

The outer shaft 110 can be evaluated with a three-point bending value. Here, the three-point bending refers to the maximum load when immersed in water at 37° C. for 30 minutes and then pushed with a support base of R=2 mm and a pusher with a distance between the support stand of 25.4 mm and a test speed of 5 mm/min.

When the outer diameter of the outer shaft 110 is, the three-point bending value is preferably 50 gf (gram-force) to 800 gf. If the three-point bending value is 50 gf or less, the outer shaft 110 hangs down and does not form a spiral. When the three-point bending value of the outer shaft 110 exceeds 800 gf, the outer shaft 110 is in a rolled state, so it does not become a three-dimensional helical structure. In the case where the outer shaft 110 is a single body, if outer diameter is 2.5 mm and inner diameter is 2.2 mm, the three-point bending value is 300 gf to 700 gf, the three-dimensional helical structure is obtained as a single body. In accordance with an embodiment, the three-point bending value of the outer shaft 110 may be determined by a flexural modulus measured by the same method, and the three-point bending value is preferably temporarily 110 MPa (mega pascal) to 260 MPa.

On the other hand, when the outer shaft 110 is used by inserting the inner shaft 210 of the dilator having the three-dimensional spiral shape or the inner catheter 200 into the lumen of the outer shaft 110, the dilator and the inner shaft 210 form a three-dimensional spiral shape, three-dimensional helical structure is not obtained as a single body. The three-point bending value is preferably 50 gf or more and 200 gf or less. In accordance with an embodiment, the three-point bending value of the outer shaft 110 may be determined by a flexural modulus measured by the same method, and the three-point bending value is preferably 30 MPa (mega pascal) to 300 MPa.

In accordance with an exemplary embodiment, the bending moment (M), for example, of the outer shaft 110, can be calculated as follows:

$$M = FL/4 = EI$$

$$I = \pi(D^4 - d^4)/64$$

where:
M=Bending moment;
I=Sectional moment of inertia of area;
E=Apparent flexural modulus;
D=Outer diameter (mm);
d=Inner diameter (mm);
L=Distance between fulcrums (mm);
F (N)=Load;
F is the load when the catheter is deflected by pushing the pusher by 1 mm; and
1000 gf=9.8 N.

In addition, the outer shaft 110 may have a marker (not illustrated) having X-ray contrast property at a distal end portion of the outer shaft 110.

Next, the hub 120 will be described.

The hub 120 includes: a hollow outer hub body portion 121 to which the outer shaft 110 is fixed; a strain relief 122 which covers a connecting portion between the outer shaft 110 and the outer hub body portion 121 and suppresses generation of kinking of the outer shaft 110 at the connecting portion; a plurality (two in the present embodiment) of wings 123 protruding radially outward from an outer circumferential surface of the outer hub body portion 121; and a protrusion 124 provided at a proximal end portion of the outer hub body portion 121 and protruding radially outward from the outer circumferential surface of the outer hub body portion 121.

The outer hub body portion 121 has a lumen 121a formed over the entire length of the outer hub body portion 121. The lumen 121a communicates with the lumen 110a of the outer shaft 110. The protrusion 124 can be screwed into a helical groove 222 of the hub 220 of the inner catheter 200 to be described later. When inserting the catheter assembly 10 into the body, the surgeon inserts the inner catheter 200 into the outer catheter 100 and rotates the hub 120 of the outer catheter 100 with respect to the hub 220 of the inner catheter 200. As a result, the protrusion 124 is screwed into the helical groove 222, and the inner catheter 200 is fixed to the outer catheter 100.

The hub 120 material is not particularly limited, for example, various thermoplastic elastomers such as a styrene type, a polyolefin type, a polyurethane type, a polyester type, a polyamide type, a polybutadiene type, a trans polyisoprene type, a fluorine rubber type, a chlorinated polyethylene type, and a combination of two or more kinds of these (a polymer alloy, a polymer blend, a multilayer body, or the like) can be used.

Inner Catheter

The inner catheter 200 includes an elongated inner shaft 210 and a hub 220 that is fixed to a proximal end portion of the inner shaft 210 and configured to be held and operated by the surgeon. Hereinafter, each part of the inner catheter 200 will be described.

First, the inner shaft 210 will be described.

The inner shaft 210 includes a tubular member having flexibility (i.e., flexible tubular member). The inner shaft 210 has a lumen 210a formed over the entire length. As illustrated in FIG. 2, a guide wire GW can be inserted into the lumen 210a.

The inner shaft 210 has a length L1 from the distal end of the inner shaft 210 to the distal end of the hub 220 in a straight state (hereinafter simply referred to as "length L1") from the distal end of the inner shaft 210 in a straight state so that the distal end of the inner shaft 110 inserted from the artery of the arm reaches the blood vessel of the lower limb. Referred to as "the length L2 of the inner shaft 210", see FIG. 1), the length L2 of the inner shaft 210 is preferably, for example, 1300 mm to 2600 mm, and more preferably 1600 mm to 2100 mm.

The inner shaft 210 may be appropriately determined according to the size of the human body, but in the case of introduction from the radial artery, the length L2 of the inner shaft 210 is preferably, for example, 1300 mm to 1500 mm to reach the iliac artery, from 1500 mm to 1700 mm to reach the superficial femoral artery, and from 1700 mm to 1900 mm to reach the popliteal artery.

The inner shaft 210 can be evaluated with a three-point bending value in the same way as the outer shaft 110. When the outer diameter of the inner shaft 210 is 2.1 mm and the inner diameter is 1.1 mm, the three-point bending value of the inner shaft 210 is preferably 100 gf to 800 gf. When the three-point bending value of the inner shaft 210 is 100 gf or less, the inner shaft 210 hangs down, does not form a spiral, and when the three-point bending value of the inner shaft 210 exceeds 800 gf, the inner shaft does not drip in a rolled state, so it does not become a three-dimensional helical structure. When the three-point bending value of the inner shaft 210 is 300 gf to 700 gf, when the inner shaft 210 is inserted into a lumen of the outer shaft 110 which is not a three-dimensional helical structure as a single body, the inner shaft 210 is three-dimensionally shape, which is preferable because the inner shaft 210 has a spiral shape. In accordance with an embodiment, the three-point bending value of the inner shaft 210 may be determined by a flexural modulus measured by the same method, and the three-point bending value is preferably 30 MPa to 280 MPa, and more preferably 100 MPa to 250 MPa.

The inner shaft 210 is insertable into the lumens 110a and 121a of the outer catheter 100. In general, as the length of the catheter in the longitudinal direction is longer, a pushing force of the surgeon on the proximal end side is less likely to be transmitted to the distal end side. In the catheter assembly 10 according to the present embodiment, the surgeon delivers the catheter assembly 10 to a target site in the blood vessel while the inner catheter 200 is inserted into the outer catheter 100. When the surgeon pushes the catheter assembly 10, the inner catheter 200 supports the outer catheter 100 from the inner side, so that the pushing force of the surgeon on the proximal side is easily transmitted to the distal end side. Thus, the surgeon can relatively easily deliver the catheter assembly 10 to the target site of the lower limb via the artery of the arm.

Figure 3A:
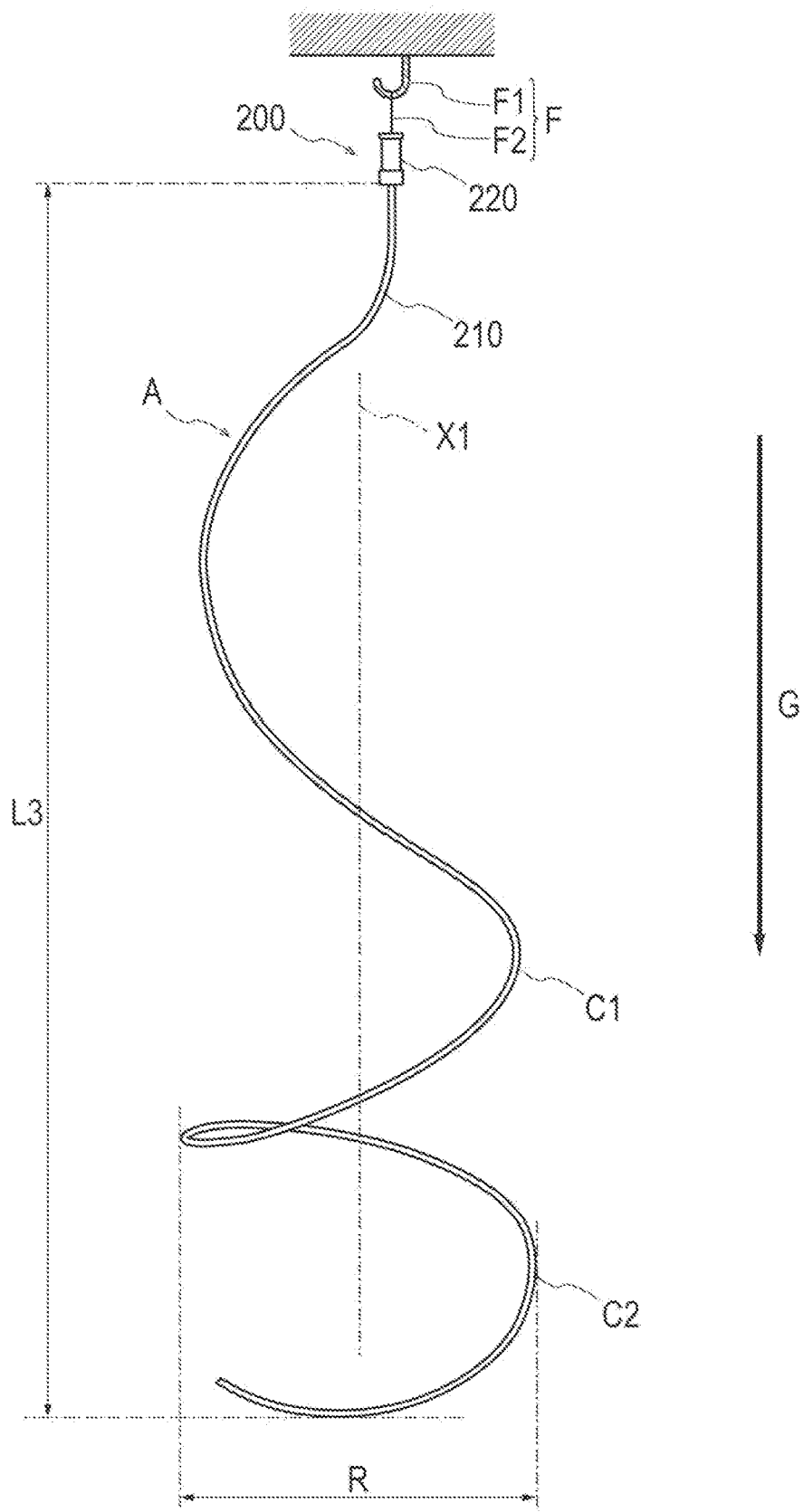
FIG. 3A is a view illustrating a state where an inner catheter provided in the catheter assembly according to the embodiment is suspended.

A part A of the inner shaft 210 (see FIG. 1, hereinafter referred to as a "wound portion A") forms a wound first shape in a state where the inner shaft 210 is suspended in a gravity direction G by holding the hub 220 as illustrated in FIG. 3A.

The "state where the inner shaft 210 is suspended in the gravity direction G by holding the hub 220" can be formed, for example, by holding the hub 220 with a holding tool F fixed to the ceiling and causing the inner shaft 210 to be suspended in the gravity direction G. In FIG. 3A, the holding tool F is constituted by a hook F1 fixed to the ceiling and a cord F2 hooked by the hook F1 and wound around the proximal end side of the hub 220, but the configuration of the holding tool F is not particularly limited as long as the holding tool can hold the hub 220.

The first shape is not particularly limited as long as the shaft is wound and a length L3 of the inner shaft 210 along the gravity direction G (see FIG. 3A) is longer than a length L4 (see FIG. 5) of the inner shaft 210 along the gravity direction G in a placed state to be described later. Thus, examples of the first shape include a three-dimensional helix and a shape having both a three-dimensional helix and a two-dimensional spiral, and the like, but do not include a "C shape" in which a central portion of the inner shaft 210 is just bent when the inner shaft 210 in the suspended state is viewed in a front view, a "J shape" in which the distal end portion of the inner shaft 210 is just curved, a shape with the "only two-dimensional spiral", and the like. In the present embodiment, the first shape is a three-dimensional helix formed around an axis X1 along the gravity direction as illustrated in FIG. 3A. In the present embodiment, the wound portion A in the first shape is in the state of being wound around the axis X1 by about two and one quarter turns in which portions (for example, C1 and C2) adjacent to each other in the direction of the axis X1 are separated from each other in the direction of the axis X1. In the present embodiment, the axis X1 of the helix extends along the gravity direction G, but does not need to extend along the gravity direction G, and may be inclined with respect to the gravity direction G.

Figure 3B:
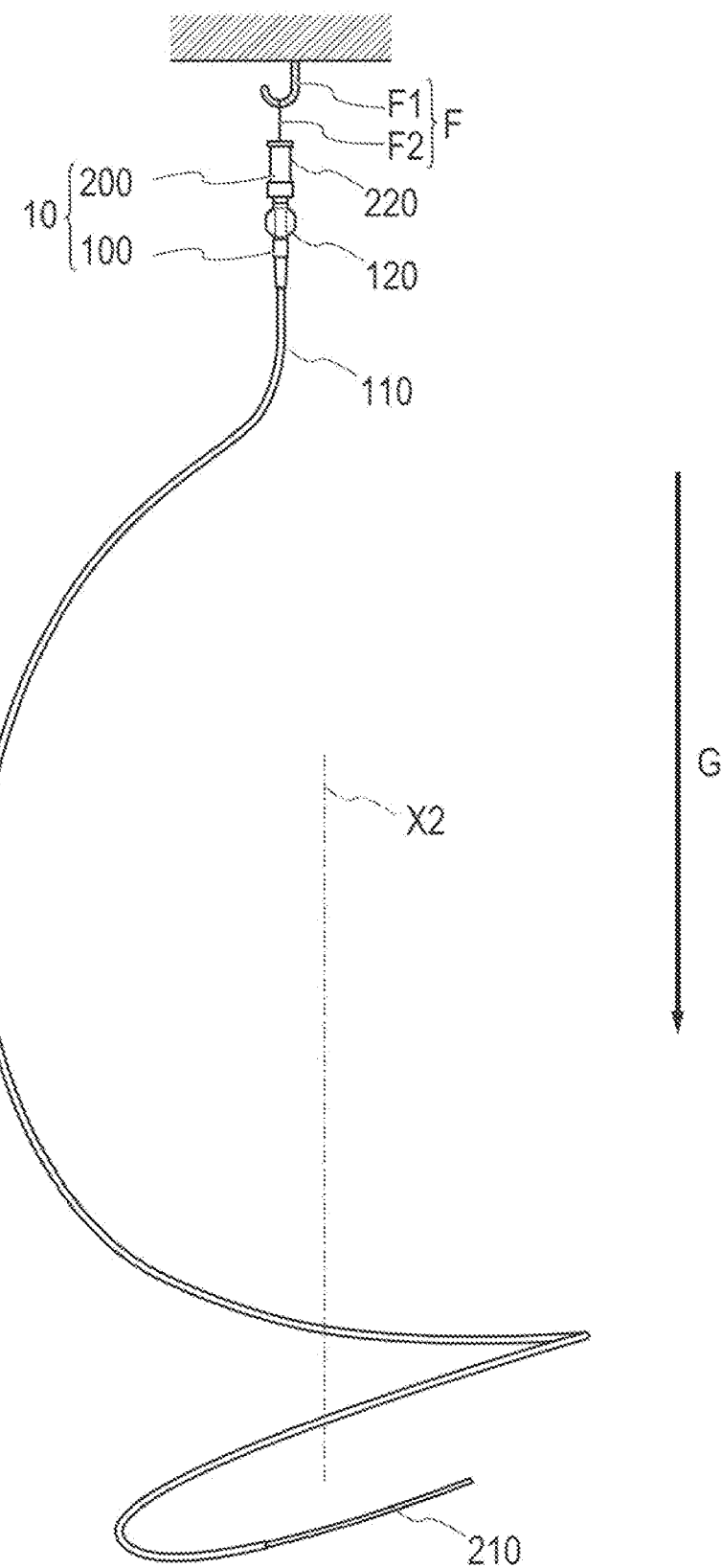
FIG. 3B is a view illustrating a state where the catheter assembly according to the embodiment is assembled and suspended.

In this manner, the wound portion A forms the first shape in the suspended state. In addition, the catheter assembly 10 forms a wound third shape in which the outer catheter 100 not having the wound shape and the inner catheter 200 having the first shape are combined in a state where the inner catheter 200 is inserted into the outer catheter 100, and the outer shaft 110 and the inner shaft 210 are suspended by holding the hub 220 as illustrated in FIG. 3B. Thus, for example, when the surgeon holds and manipulates the proximal end side of the inner catheter 200 or the catheter assembly 10, the inner catheter 200 or the catheter assembly 10 forms the wound shape and becomes compact in the gravity direction G without being wound by the surgeon. Thus, the inner catheter 200 and the catheter assembly 10 can help reduce the risk of being in contact with an unclean surface such as a floor, and it becomes unnecessary or rather easy for the surgeon to perform work of bundling the inner catheter 200 and the catheter assembly 10 with a clip or the like so as to prevent the catheter 200 from coming into contact with the unclean surface such as the floor. Although the third shape formed by the catheter assembly 10 is the three-dimensional helix, wound around an axis X2 along the gravity direction G with the number of turns reduced as compared with the first shape of the inner shaft 210 in the present embodiment, the third shape is not particularly limited as long as the third shape is the wound shape. For example, the axis X2 may be inclined with respect to the gravity direction G.

In the state where the inner shaft 210 is suspended, at least a part of the inner shaft 210 may form the first shape, and it is preferable that a half or more of the distance from the distal end of the inner shaft 210 to the distal end of the hub 220 forms the first shape. The wider a region of the inner shaft 210 forming the first shape becomes, the more compact the inner shaft 210 becomes in the gravity direction G. In the present embodiment, the wound portion A is a portion excluding the distal end portion of the inner shaft 210 and the vicinity of the distal end of the hub 220 as illustrated in FIG. 1. A range of the distal end portion is not particularly limited, but can be set, for example, to a range of about from 0 mm to 400 mm, and preferably about from 0 mm to 150 mm, from the most distal end to the proximal end side. A range of the vicinity of the most distal end of the hub 220 is not particularly limited, but can be set, for example, to a range of about from 0 mm to 400 mm, and preferably about from 0 mm to 150 mm, from the most distal end to the distal end side of the hub 220.

The inner shaft 210 is not particularly limited, but can be set such that a maximum length (a maximum outer diameter R of the helix) in a direction perpendicular to the gravity direction G is equal to or longer than 1/10 and equal to or smaller than 1/3 of a length L2 (hereinafter simply referred to as the "length L2 of the inner shaft 210", see FIG. 1) from the distal end of the inner shaft 210 to the distal end of the hub 220 in the straight state as illustrated in FIG. 3A. When the maximum outer diameter R of the helix is set, for example, to be equal to or longer than 1/10 of the length L2 of the inner shaft 210 as described above, the inner shaft 210 becomes more compact in the gravity direction G in the suspended state. In addition, when the maximum outer diameter R of the helix is set, for example, to be equal to or smaller than 1/3 of the length L2 of the inner shaft 210 as described above, it is possible to suitably impart a curl to the inner shaft 210 to form the first shape.

A length L3 (helical length L3 of the inner shaft 210, see FIG. 3A) along the gravity direction G of a portion of the inner shaft 210 exposed from the hub 220 in the suspended state is not particularly limited, but is preferably equal to or smaller than 2/3 of the length L2 of the inner shaft 210, for example. Further, the helical length L3 of the inner shaft 210 is not particularly limited, but can be 30% to 50% of the length L2 of the inner shaft 210, for example. When the helical length L3 of the inner shaft 210 is set in this manner, the inner shaft 210 becomes even more compact in the gravity direction G.

Figure 4A:
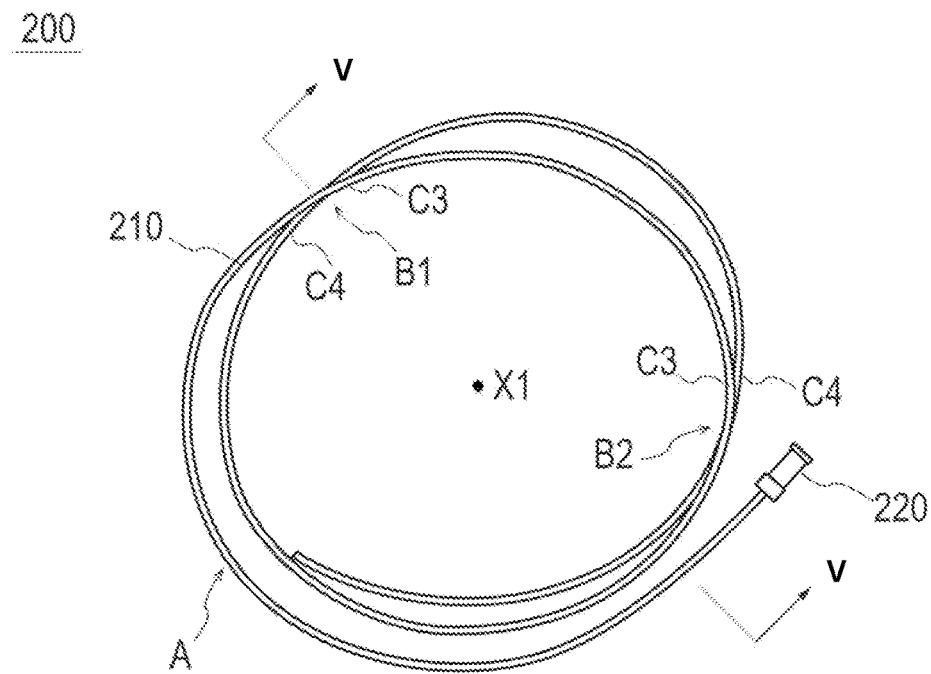
FIG. 4A is a view illustrating a state where the inner catheter according to the embodiment is placed on a reference plane.
Figure 5:
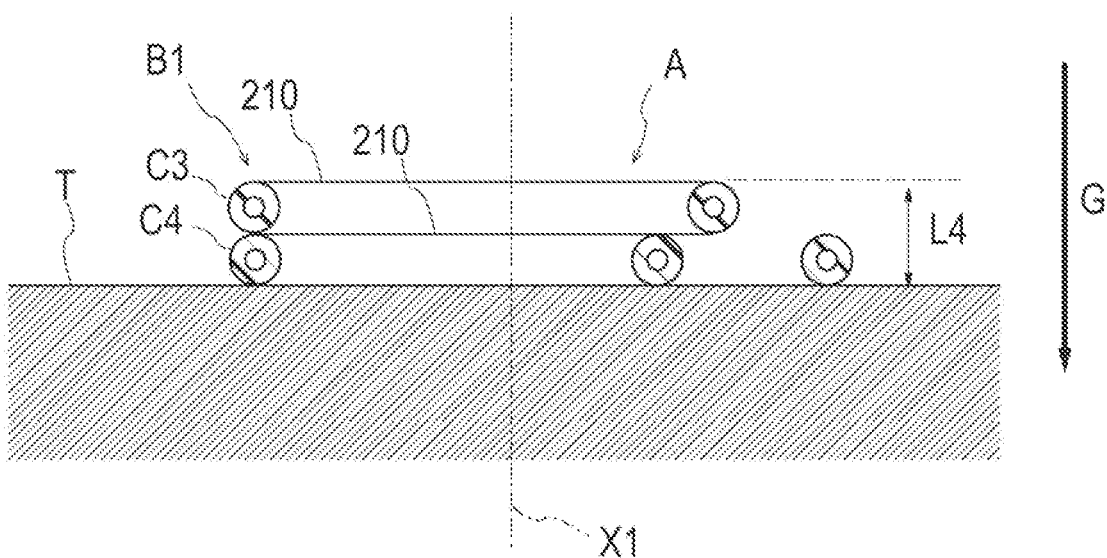
FIG. 5 is a cross-sectional view taken along a line V-V of FIG. 4A.
Figure 6:
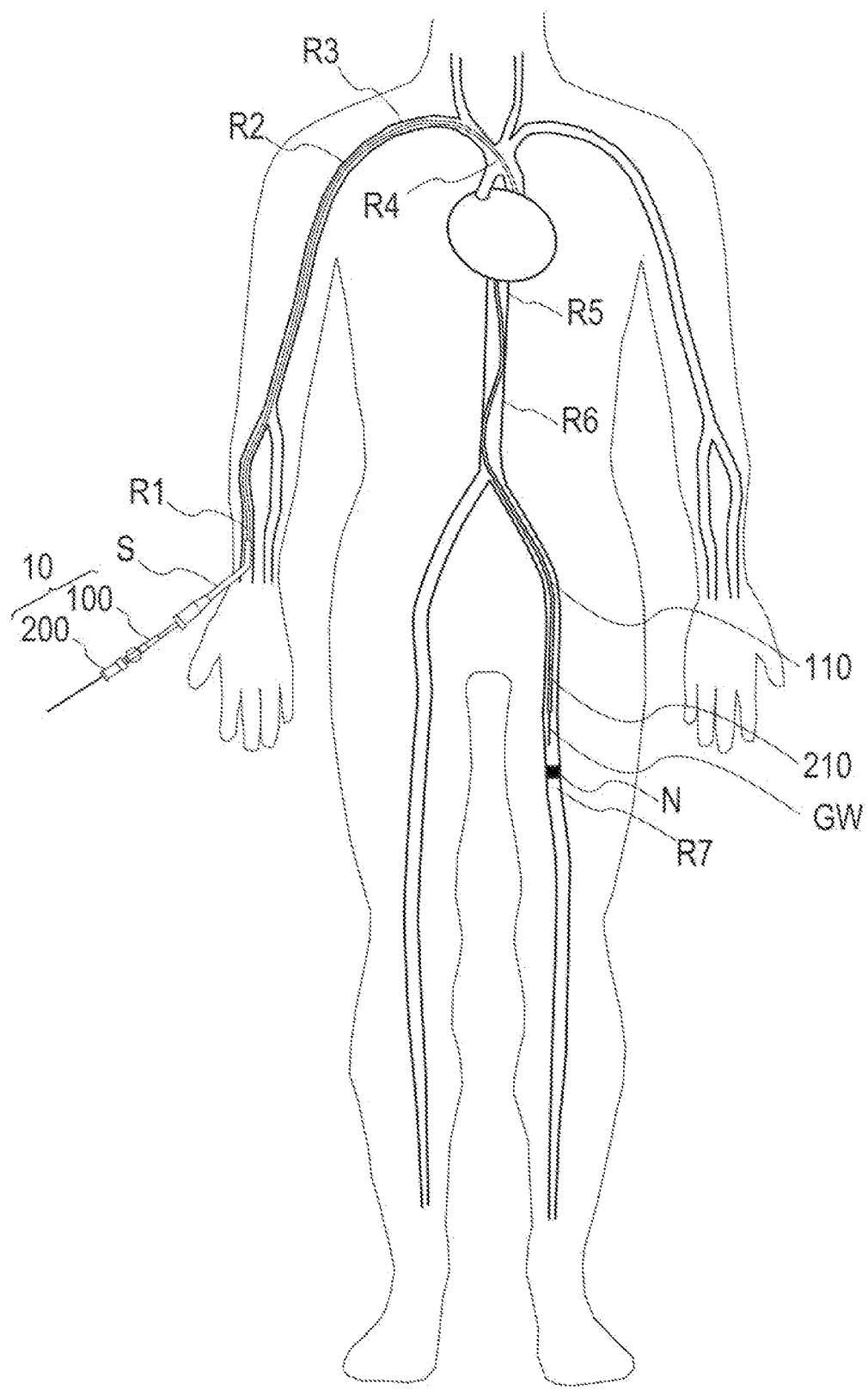
FIG. 6 is a schematic view for describing a technique using the catheter assembly according to the embodiment.

As illustrated in FIGS. 4A and 5, the wound portion A is wound and forms a second shape in which the length L4 of the inner shaft 210 along the gravity direction G is shorter than the length L3 of the inner shaft 210 along the gravity direction G in the first shape in a state where the inner catheter 200 is placed on a flat reference plane T perpendicular to the gravity direction G.

Figure 4B:
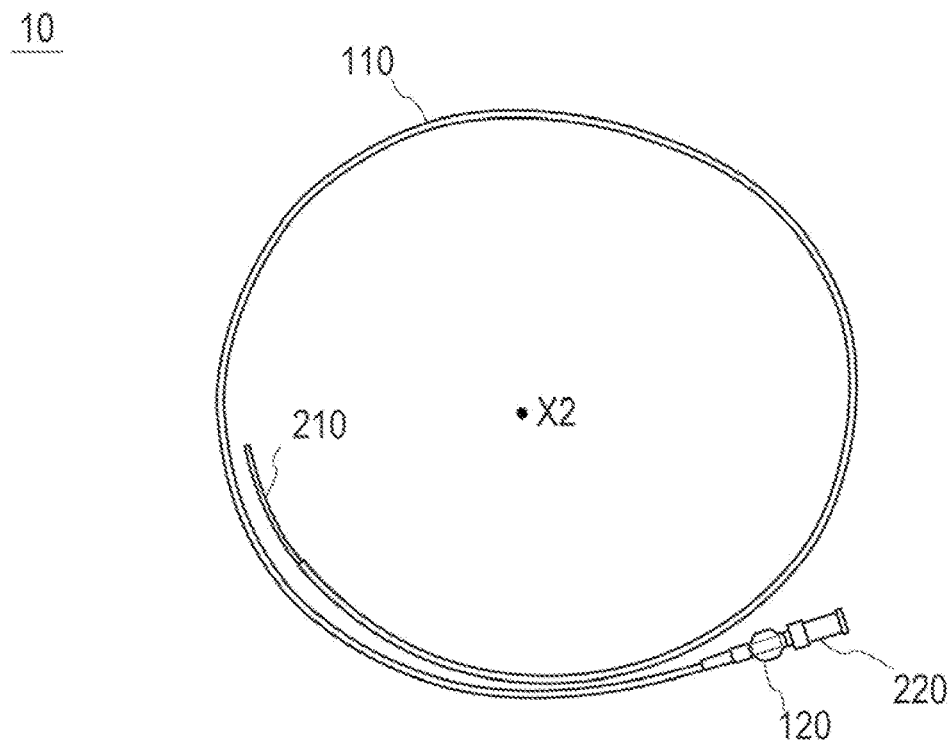
FIG. 4B is a view illustrating a state where the catheter assembly according to the embodiment is assembled and placed on the reference plane.

As illustrated in FIG. 5, the "state of being placed on the reference plane T" means a state where the inner catheter 200 is placed on the reference plane T and the inner catheter 200 is in contact with no part other than the reference plane T. That is, an external force does not act on the inner catheter 200 except for gravity and a force caused by the contact with the reference plane T (a frictional force against the reference plane T and a resistance from reference plane T) in this state. In this manner, the wound portion A forms the second shape in the placed state without being wound by the surgeon. In addition, the catheter assembly 10 also forms a fourth shape in which the outer shaft 110 and a part of the inner shaft 210 are wound with the smaller number of turns than the second shape by combining the outer catheter 100 without the wound shape and the inner catheter 200 with the second shape in the placed state as illustrated in FIG. 4B. Before inserting the catheter assembly 10 into the blood vessel of the patient, the surgeon fills a medical tray or the like with a priming solution, and performs priming work of immersing the inner catheter 200 and the catheter assembly 10 in the priming solution. In addition, there is a case where the inner catheter 200 or the catheter assembly 10 is temporarily placed on a table, the medical tray, or the like during a procedure. In such a case, the inner catheter 200 or the catheter assembly 10 forms a wound shape on the table or the medical tray without being wound by the surgeon, and becomes compact in the gravity direction G. In this manner, the surgeon does not need to wind the inner catheter 200 or the catheter assembly 10 such that the inner catheter 200 or the catheter assembly 10 does not become a hindrance or fits in the medical tray.

The second shape is not particularly limited as long as the catheter is wound and the length L4 (see FIG. 5) of the inner shaft 210 along the gravity direction G is shorter than the length L3 (see FIG. 3A) of the inner shaft 210 along the gravity direction G in the suspended state. Thus, examples of the first shape include a "two-dimensional spiral", an "a shape" of being wound by one turn when the reference plane T is viewed from above, and a "C shape" of being bent so as to surround the axis X1 when the reference plane T is viewed from above, and the like.

In the present embodiment, the second shape is a shape obtained by winding the catheter around the axis X1 about two and a quarter turns when the reference plane T is viewed from above as illustrated in FIG. 4A. In addition, in the second shape, the inner shaft 210 has overlapping portions B1 and B2 in which wound portions C3 and C4 overlap each other when the reference plane T is viewed from above. As illustrated in FIG. 5, the wound portions C3 and C4 abut on each other in the overlapping portions B1 and B2 (although only the overlapping portion B1 is illustrated in the drawing). In this manner, since the adjacent portions C3 and C4 abut on each other in the overlapping portions B1 and B2, the inner catheter 200 becomes even more compact in the gravity direction G. Incidentally, the inner catheter 200 may be configured such that the length L4 of the inner shaft 210 along the gravity direction G in the placed state is shorter than the length L3 (see FIG. 3A) along the gravity direction G of the inner shaft 210 in the suspended state, and the adjacent portions C3 and C4 may be slightly separated from each other without abutting on each other.

Although a method of imparting the curl to the inner shaft 210 to form the first shape and the second shape is not particularly limited, it is possible to use, for example, a method of winding the inner shaft 210 along an annular jig or a columnar jig and maintaining the state for a predetermined time, or the like. Incidentally, when the inner shaft 210 is inserted into the outer shaft 110 to which no curl is imparted, it is preferable that the catheter assembly 10 has a strong curl (shape retention property) to the extent that a wound shape (the above-described third or fourth shape) can be formed in the suspended state or placed state while being loosened due to the shape of the outer shaft 110 to which no curl is imparted.

The inner shaft 210 is preferably made of a resin material. When the inner shaft 210 is made of the resin material, it is possible to suitably impart the curl to the inner shaft 210 by the above-described method. Although the resin material forming the inner shaft 210 is not particularly limited, it is possible to use, for example, the same resin material as the outer layer 113 of the outer catheter 100 described above. In addition, the inner shaft 210 may have a hydrophilic coating layer on an outer surface on the distal end side of the inner shaft 210.

Incidentally, the inner shaft 210 may have a marker (not illustrated) having X-ray contrast property at a distal end portion of the inner shaft 210.

The length L2 of the inner shaft 210 can be set to be longer than the length L1 of the outer shaft 110. With this configuration, the distal end portion of the inner shaft 210 can be exposed from a distal end opening of the outer shaft 110 in the state of being inserted into the outer shaft 110 (see FIG. 6).

Next, the hub 220 will be described.

As illustrated in FIG. 1, the hub 220 has a hollow inner hub body portion 221 and a helical groove 222 provided on an inner surface of the inner hub body portion 221. The inner hub body portion 221 has a lumen 221a formed over the entire length of the inner hub body portion 221. The lumen 221a communicates with the lumen 210a of the inner shaft 210.

The hub 220 material is not particularly limited, for example, the same material as the hub 120 of the outer catheter 100 can be used.

Use Example

Next, a description will be given regarding a use example of the catheter assembly 10 in which the catheter assembly 10 is applied to a procedure for treating a lesion (stenosis N) generated in a left superficial femoral artery (SFA) R7 of a lower limb via a radial artery R1 of a right arm of a patient with reference to FIG. 6. The catheter assembly 10 can be evaluated with a three-point bending value obtained by the same method as the outer shaft 110 and the inner shaft 210. In the case of an outer diameter of 2.4 mm and an inner diameter of 1.1 mm, the three-point bending value of the catheter assembly 10 is 150 gf to 1000 gf, more preferably 300 gf to 800 gf, more preferably 350 gf to 650 gf. If the three-point bending value of the catheter assembly 10 is 150 gf or less, the catheter assembly 10 hangs down and does not form a helix, and when the three-point bending value of the catheter assembly 10 exceeds 1000 gf, the catheter assembly 10 does not drip in a rolled state and does not have a three-dimensional helical structure. When the three-point bending value of the catheter assembly 10 is 300 gf to 700 gf, when the inner shaft 210 is inserted into a lumen of the outer shaft 110 which is not a three-dimensional helical structure as a single body, the inner shaft 210 is three-dimensionally it is preferable because it has a spiral shape. Alternatively, it may be determined by the flexural modulus measured by the same method, and it is preferable that the apparent flexural modulus when the outer diameter is 2.4 mm and the inner diameter is 1.1 mm is preferably 40 MPa to 320 MPa, more preferably 90 MPa to 250 MPa, and most preferably 100 MPa to 210 MPa.

First, the surgeon places the outer catheter 100 and the inner catheter 200 on a medical tray, and performs the priming work of immerging the outer catheter 100 and the inner catheter 200 in the priming solution.

Next, the surgeon inserts the inner catheter 200 into the outer catheter 100 and screws the protrusion 124 of the outer catheter 100 into the helical groove 222 of the inner catheter. As a result, when the catheter assembly 10 is inserted into the blood vessel of the patient, the surgeon can integrally operate the outer catheter 100 and the inner catheter 200, thereby facilitating the operation. The surgeon can temporarily place the assembled catheter assembly 10 on the medical tray or the like until the catheter assembly 10 is used again.

Next, the surgeon punctures the radial artery R1 of the right arm with the introducer sheath S and causes the introducer sheath S to remain in the radial artery R1 as illustrated in FIG. 6. As a result, the surgeon can secure an introduction path for introducing the catheter assembly 10 into the radial artery R1.

Next, the surgeon inserts the catheter assembly 10 into the introducer sheath S in a state where the guide wire GW has been inserted into the lumen of the catheter assembly 10. Then, the surgeon introduces the catheter assembly 10 into the radial artery R1 along the guide wire GW.

Next, the surgeon pushes the catheter assembly 10 to proceed along the preceding guide wire GW to a target site (for example, the vicinity of the upper part of the left superficial femoral artery (SFA) R7) in front of the stenosis N. Since the catheter assembly 10 has the wound shape, the surgeon can easily move the catheter assembly 10 to proceed along a curved artery such as a right subclavian artery R2, a brachiocephalic artery R3, and an aortic arch R4, or the like. In addition, the surgeon can push the catheter assembly 10 forward such that the outer catheter 100 draws a helix while abutting on wall surfaces of a thoracic aorta R5 and an abdominal aorta R6 since the catheter assembly 10 has the wound shape.

Next, after the distal end of the catheter assembly 10 reaches the target site, the surgeon releases the screwing between the helical groove 222 of the inner catheter 200 and the protrusion 124 of the outer catheter 100. Then, the surgeon removes the inner catheter 200 out of the body while leaving the outer catheter 100 and the guide wire GW in the blood vessel.

Next, the surgeon inserts a balloon catheter (not illustrated) having an expanded portion, which is expandable and contractible, at a distal end of the balloon catheter into the lumens 110a and 121a of the outer catheter 100 along the guide wire GW. Further, the surgeon pushes the balloon catheter into the lumens 110a and 121a of the outer catheter 100 such that the expanded portion protrudes from the distal end of the outer catheter 100 and the expanded portion is arranged at the stenosis N. Incidentally, since the catheter assembly 10 abuts on the wall surfaces of the thoracic aorta R5 and the abdominal aorta R6 while drawing the helix as described above, a contact area between the outer catheter 100 and a blood vessel wall is wide. Thus, even if a reaction force caused by pushing the balloon catheter forward is transmitted to the outer catheter 100, it is possible to suitably suppress the movement of the outer catheter in a direction of being removed out of the body due to a frictional force between the outer catheter 100 and each wall surface of the thoracic aorta R5 and the abdominal aorta R6.

Next, the surgeon expands the expanded portion of the balloon catheter to push and dilate the stenosis N. Next, the surgeon contracts the expanded portion of the balloon catheter and removes the balloon catheter and the guide wire GW out of the body.

Next, the surgeon removes the outer catheter 100 out of the body. Next, the surgeon removes the introducer sheath S out of the body and stops bleeding of a puncture site.

Although the use example of the catheter assembly 10 has been described above, the procedure to which the catheter assembly 10 is applied is not limited to the above-described procedure. For example, a site to be pierced is not limited to the radial artery R1 of the right arm, but may be a radial artery of a left arm, for example. In addition, the lesion is not limited to one generated in the left superficial femoral artery R7, but may be those generated in, for example, a right superficial femoral artery, right and left iliac arteries, and right and left popliteal arteries. In addition, the treatment to be performed via the outer catheter 100 is not limited to the treatment using only the balloon catheter. For example, a stent may be arranged on an outer surface of a balloon. In addition, a long object such as a catheter other than the balloon catheter, an endoscope, an ultrasonic probe, and a temperature sensor may be inserted or removed via the outer catheter 100, and various liquids such as a contrast agent (X-ray contrast agent), a medical solution, and saline may be injected.

The above-described inner catheter 200 according to the present embodiment includes the elongated inner shaft 210 to be inserted into the blood vessel and the hub 220 to be connected to the proximal end side of the inner shaft 210. The inner shaft 210 forms the first shape in which at least the part A of the inner shaft 210 is wound in the state where the inner shaft 210 is suspended in the gravity direction G by holding the hub 220. In the state where the hub 220 and the inner shaft 210 are placed on the flat reference plane T perpendicular to the gravity direction G, the inner shaft 210 forms the second shape in which at least the part A of the inner shaft 210 is wound and the length L4 of the inner shaft 210 along the gravity direction G is shorter than the length L3 along the gravity direction G of the inner shaft 210 in the first shape.

According to the inner catheter 200 configured as described above, when the surgeon holds and manipulates the proximal end side of the inner catheter 200, at least the part A of the inner shaft 210 is wound to form the first shape and becomes compact. Thus, the risk of the inner catheter 200 being in contact with an unclean surface such as a floor is reduced, and it becomes unnecessary or rather easy for the surgeon to perform work of bundling the inner catheter 200 with a clip or the like so as to prevent the contact with the unclean surface such as the floor. In addition, when the surgeon places the inner catheter 200 on a medical tray, a table, or the like, at least the part A of the inner shaft 210 forms the second shape and becomes more compact than the first shape. In this manner, it is possible to provide the inner catheter 200 which is rather easy to handle.

In addition, the first shape is the three-dimensional helix. Thus, the inner shaft 210 becomes compact in the gravity direction G in the suspended state.

In addition, the second shape has the overlapping portions B1 and B2 in which the wound portions C3 and C4 of the inner shaft 210 overlap each other when the reference plane T is viewed from above. In the overlapping portions B1 and B2, the wound portions C3 and C4 abut on each other. Thus, when the surgeon has placed the inner catheter 200 on the medical tray, the table, or the like, the inner shaft 210 becomes compact.

In addition, in the state where the hub 220 is held and the inner shaft 210 is suspended, a portion, which is a half or more of the inner shaft 210 from the distal end of the inner shaft 210 to the distal end of the hub 220 forms the first shape, and a maximum length R of the inner shaft 210 in the direction perpendicular to the gravity direction G in the first shape is equal to or longer than ⅒ and equal to or smaller than ⅓ of the length L2 from the distal end of the inner shaft 210 to the distal end of the hub 220 in the straight state. When being set as described above, the inner shaft 210 becomes even more compact in the gravity direction G, and it is also possible to suitably impart the curl to the inner shaft 210 to form the first shape.

In addition, the length L3 of the portion of the inner shaft 210 exposed from the hub 220 along the gravity direction G in the first shape is equal to or smaller than ⅔ of the length L2 of the inner shaft 210 from the distal end of the inner shaft 210 to the distal end of the hub 220 in the straight state. When being set as described above, the inner shaft 210 becomes even more compact in the gravity direction G.

In addition, the catheter assembly 10 according to the present embodiment includes the outer catheter 100 and the inner catheter 200 that is insertable into the outer catheter 100. The outer catheter 100 and inner catheter 200 include the elongated shafts 110 and 210 and the hubs 120 and 220 connected to the shafts 110 and 210, respectively. The inner shaft 210 of the inner catheter 200 forms the first shape in which at least the part A of the inner shaft 210 is wound in the state where the inner shaft 210 is suspended in the gravity direction G by holding the hub 220. The third shape is formed in which a part of the shafts of the outer catheter 100 and the inner catheter 200 is wound in the state where the inner catheter 200 is inserted into the outer catheter 100, and the shafts 110 and 210 of the outer catheter 100 and the inner catheter 200 are suspended in the gravity direction G by holding the hub 220 of the inner catheter 200.

According to the catheter assembly 10 configured as described above, when the surgeon holds and manipulates the proximal end side of the catheter assembly in the state where the inner catheter is inserted into the outer catheter, at least a part of the shaft of the catheter assembly is wound to form the third shape and becomes compact. Thus, the risk of the catheter assembly being in contact with an unclean surface such as a floor is reduced, and it becomes unnecessary or easy for the surgeon to perform work of bundling the catheter with a clip or the like so as to prevent the contact with the unclean surface such as the floor. In this manner, it is possible to provide the catheter assembly which is relatively easy to handle.

Modified Example

Figure 7:
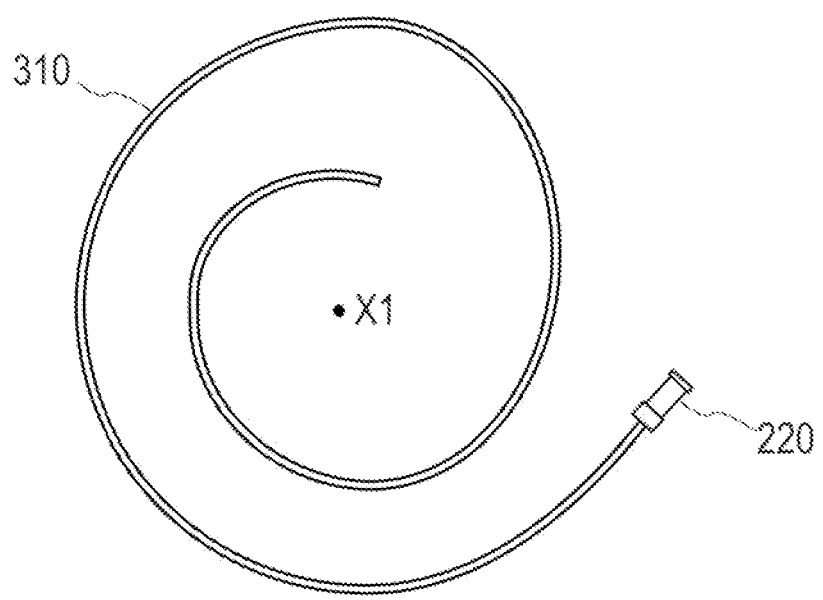
FIG. 7 is a view illustrating a state where an inner catheter according to a modified example is placed on a reference plane.

FIG. 7 is a view illustrating an inner shaft 310 according to a modified example. Hereinafter, the inner shaft 310 according to the modified example will be described.

The inner shaft 310 according to the modified example is different from that of the above embodiment in terms of a shape (second shape) in a state of being placed on the reference plane T. Since the other configurations are the same as those in the above embodiment, the description of the other configurations will be omitted.

A second shape of the inner shaft 310 is a two-dimensional spiral. In this manner, the second shape is wound on the reference plane T (that is, wound on a two-dimensional plane) without having an overlapping portion in which wound portions of the inner shaft 310 overlap each other when the reference plane T is viewed from above.

Thus, the inner shaft 210 becomes even more compact in the gravity direction G as compared with the inner shaft 210 according to the above embodiment.

Although the catheter and the catheter assembly according to the present invention have been described through the embodiments as above, the present invention is not limited to only the configurations that have been described in the specification but can be appropriately changed based on the description of the claims.

For example, the above embodiment has been described by exemplifying the inner catheter of the guiding catheter as the catheter to which the present invention is applied. However, the invention is not limited thereto, and can be applied to, for example, an introducer sheath, a dilator, a guiding sheath, a angiographic catheter, a medical solution administration catheter, and the like.

In addition, the above embodiment has been described by exemplifying the guiding catheter having a dual structure that includes the outer catheter and the inner catheter as the catheter assembly to which the present invention is applied. However, the invention is not limited to the above embodiments, and can be applied to, for example, an introducer including an introducer sheath (corresponding to the "outer catheter") and a dilator (corresponding to the "inner catheter").

In addition, the mode in which the inner catheter forms the first shape and the second shape has been described in the above embodiment, but the inner catheter does not necessarily form the first shape and the second shape and the outer catheter may form the first shape and the second shape, or both the inner catheter and the outer catheter may form the first shape and the second shape.

The detailed description above describes a catheter and a catheter assembly. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A treatment method comprising:
preparing a catheter assembly by inserting an inner catheter into an outer catheter and screwing a protrusion of the outer catheter into a helical groove of the inner catheter;
inserting a guide wire into a lumen of the inner catheter of the catheter assembly such that the guide wire protrudes from a distal end of the inner catheter;
inserting the catheter assembly into an introducer sheath, the introducer sheath configured to pierce through and remain in a radial artery of a living body, in a state where the guide wire is inserted into a lumen of the catheter assembly;
introducing the catheter assembly into the radial artery along the guide wire;
pushing the catheter assembly along the guide wire to a target site in front of a stenosis of a blood vessel;
releasing the screwing between the helical groove of the inner catheter and the protrusion of the outer catheter after a distal end of the catheter assembly reaches the target site;
removing the inner catheter from the living body while leaving the outer catheter and the guide wire in the blood vessel;
inserting a treatment device along the guide wire into a lumen of the outer catheter; and
causing the outer catheter to abut on at least a part of wall surfaces of a thoracic aorta and an abdominal aorta while drawing a helix and causing the treatment device to protrude from a distal end of the outer catheter such that an expanded portion is arranged at the stenosis.

2. The method according to claim 1, wherein
the inner catheter is a flexible tubular member configured to fit within the outer catheter, the inner catheter having a lumen extending from a proximal end of the inner catheter to a distal end of the inner catheter; and
the outer catheter includes a tubular inner layer, a reinforcing member provided on an outer circumferential surface of the tubular inner layer, and an outer layer surrounding the tubular inner layer and the reinforcing member.

3. The method according to claim 1. further comprising:
applying a hydrophilic coating on one or more of an outer surface of the outer layer of the outer catheter and an outer surface of the inner catheter.

4. The method according to claim 1, further comprising:
immerging the inner catheter and the outer catheter in a priming solution prior to preparing the catheter assembly by inserting the inner catheter into the outer catheter.

5. The method according to claim 1, further comprising:
moving the catheter assembly along a curved artery to the target site, the curved artery being a right subclavian artery, a brachiocephalic artery, or an aortic arch.

6. The method according to claim 1, wherein the target site is in an iliac artery, a femoral artery, or a popliteal artery, the inner shaft having a length of 1300 mm to 1500 mm to reach the iliac artery, a length of 1500 mm to 1700 mm to reach the femoral artery, or a length of 1700 mm to 1900 mm to reach the popliteal artery.

7. The method according to claim 1, further comprising:
transmitting a reaction force to the outer catheter with the pushing of the treatment device forward along the guide wire; and
suppressing a movement of the outer catheter in a direction of being removed out of the living body caused by the reaction force by a frictional force between the outer catheter and each wall surface of the thoracic aorta and the abdominal aorta.

8. The method according to claim 1, wherein the treatment device is a balloon catheter, the method further comprises:
expanding an expanded portion of the balloon catheter to dilate the stenosis.

9. The method according to claim 8, further comprising:
contracting the expanded portion of the balloon catheter; and
removing the balloon catheter and the guide wire from the living body.

10. The method according to claim 9, further comprising:
removing the outer catheter from the living;

removing the introducer sheath from the living body; and
stopping a bleeding of a puncture site in the radial artery of the living body.

11. The method according to claim 1, wherein the inner catheter includes an elongated inner shaft and a hub, the hub being connected to a proximal end of the inner shaft, the method further comprising:
winding at least a part of the inner shaft to form a first shape in a state where the inner shaft is suspended in a gravity direction by holding the hub.

12. The method according to claim 11, further comprising:
placing the hub and the inner shaft in a state where on a flat reference plane perpendicular to the gravity direction; and
forming the inner shaft in a second shape in which at least the part of the inner shaft is wound and a length of the inner shaft along the gravity direction is shorter than a length along the gravity direction of the inner shaft in the first shape.

13. The method according to claim 12. wherein the flat reference plane perpendicular to the gravity direction is a medical tray or a table.

14. The method according to claim 11, wherein the first shape is a three-dimensional helix.

15. The method according to claim 11, wherein
a portion, which is a half or more of the inner shaft from a distal end of the inner shaft to a distal end of the hub forms the first shape in a state where the inner shaft is suspended; and
a maximum length of the inner shaft in a direction perpendicular to the gravity direction in the first shape is equal to or longer than $1/10$ and equal to or smaller than $1/3$ of a length from the distal end of the inner shaft to the distal end of the hub in a straight state.

16. The method according to claim 11, wherein a length of a portion of the inner shaft exposed from the hub along the gravity direction in the first shape is equal to or smaller than $2/3$ of the length of the inner shaft from the distal end of the inner shaft to the distal end of the hub in the straight state.

17. A treatment method comprising:
inserting an inner catheter into an outer catheter and screwing a protrusion of the outer catheter into a helical groove of the inner catheter to form a catheter assembly;
puncturing a radial artery of a living body with an introducer sheath;
inserting a guide wire into a lumen of the inner catheter;
introducing the catheter assembly along with the guide wire into the radial artery via the introducer sheath;
pushing the catheter assembly along the guide wire to a target site in a blood vessel;
releasing the screwing between the helical groove of the inner catheter and the protrusion of the outer catheter after a distal end of the catheter assembly reaches the target site;
removing the inner catheter from the living body while leaving the outer catheter and the guide wire in the blood vessel;
inserting a treatment device along the guide wire into a lumen of the outer catheter; and
causing the outer catheter to abut on at least a part of wall surfaces of a thoracic aorta and an abdominal aorta while drawing a helix and causing the treatment device to protrude from a distal end of the outer catheter at the target site.

18. The method according to claim 17, wherein
the inner catheter is a flexible tubular member configured to fit within the outer catheter, the inner catheter having a lumen extending from a proximal end of the inner catheter to a distal end of the inner catheter; and
the outer catheter includes a tubular inner layer, a reinforcing member provided on an outer circumferential surface of the tubular inner layer, and an outer layer surrounding the tubular inner layer and the reinforcing member.

19. The method according to claim 17, further comprising:
applying a hydrophilic coating on one or more of an outer surface of the outer layer of the outer catheter and an outer surface of the inner catheter.

20. The method according to claim 17, wherein
a portion, which is a half or more of the inner shaft from a distal end of the inner shaft to a distal end of the hub forms the first shape in a state where the inner shaft is suspended; and
a maximum length of the inner shaft in a direction perpendicular to the gravity direction in the first shape is equal to or longer than $1/10$ and equal to or smaller than $1/3$ of a length from the distal end of the inner shaft to the distal end of the hub in a straight state.

* * * * *